(12) United States Patent
Yaffe-Ermoza et al.

(10) Patent No.: US 8,870,765 B2
(45) Date of Patent: Oct. 28, 2014

(54) POLYGRAPH

(76) Inventors: Eyal Yaffe-Ermoza, Jerusalem (IL); Ovad Golan, Jerusalem (IL); Zeev Danieli, Jerusalem (IL); Ohad Perets, Jerusalem (IL); Shaul Bar Lev, Tel Aviv (IL); Roni Sivan, Tel Aviv (IL)

( * ) Notice: Subject to any disclaimer, the term of this patent is extended or adjusted under 35 U.S.C. 154(b) by 177 days.

(21) Appl. No.: 13/285,464

(22) Filed: Oct. 31, 2011

(65) Prior Publication Data

US 2013/0109930 A1 May 2, 2013

(51) Int. Cl.
*A61B 5/00* (2006.01)
*A61B 5/16* (2006.01)

(52) U.S. Cl.
CPC ............... *A61B 5/164* (2013.01); *A61B 5/6806* (2013.01); *A61B 5/6825* (2013.01)
USPC ........................................................ 600/301

(58) Field of Classification Search
USPC .................................................. 600/300–301
See application file for complete search history.

(56) References Cited

U.S. PATENT DOCUMENTS

| | | | | |
|---|---|---|---|---|
| 4,281,647 | A * | 8/1981 | Antypas ........................... | 602/21 |
| 6,322,515 | B1 * | 11/2001 | Goor et al. .................... | 600/485 |
| 6,415,176 | B1 * | 7/2002 | Scheirer et al. ............... | 600/547 |
| 7,340,125 | B1 * | 3/2008 | Doty .............................. | 385/16 |
| 7,565,193 | B2 * | 7/2009 | Laken ........................... | 600/544 |
| 7,899,524 | B2 * | 3/2011 | Kozel ............................ | 600/544 |
| 8,014,847 | B2 * | 9/2011 | Shastri et al. ................. | 600/410 |
| 8,099,159 | B2 * | 1/2012 | Cook ............................. | 600/547 |
| 2003/0135097 | A1 * | 7/2003 | Wiederhold et al. .......... | 600/301 |
| 2003/0149344 | A1 * | 8/2003 | Nizan ............................ | 600/300 |
| 2003/0179807 | A1 * | 9/2003 | Newman ......................... | 374/45 |
| 2004/0143170 | A1 * | 7/2004 | DuRousseau ................. | 600/300 |
| 2005/0065413 | A1 * | 3/2005 | Cacioppo et al. ............. | 600/300 |
| 2005/0143629 | A1 * | 6/2005 | Farwell .......................... | 600/300 |
| 2006/0173274 | A1 * | 8/2006 | George et al. ................. | 600/409 |
| 2007/0038035 | A1 * | 2/2007 | Ehrlich et al. ................ | 600/300 |
| 2007/0076935 | A1 * | 4/2007 | Jeung et al. ................... | 382/128 |
| 2007/0100216 | A1 * | 5/2007 | Radcliffe et al. ............. | 600/300 |
| 2007/0191691 | A1 * | 8/2007 | Polanco ........................ | 600/301 |
| 2007/0208235 | A1 * | 9/2007 | Besson et al. ................. | 600/301 |
| 2007/0249914 | A1 * | 10/2007 | Cacioppo et al. ............. | 600/300 |
| 2007/0270659 | A1 * | 11/2007 | Giegerich ..................... | 600/300 |
| 2008/0045847 | A1 * | 2/2008 | Farag et al. ................... | 600/500 |
| 2008/0171914 | A1 * | 7/2008 | Ouwerkerk et al. .......... | 600/300 |
| 2008/0260212 | A1 * | 10/2008 | Moskal et al. ................ | 382/118 |
| 2009/0033333 | A1 * | 2/2009 | Gribova et al. ............... | 324/439 |
| 2009/0080730 | A1 * | 3/2009 | Pavlidis ........................ | 382/128 |
| 2009/0216092 | A1 * | 8/2009 | Waldorf et al. ............... | 600/301 |
| 2009/0309891 | A1 * | 12/2009 | Karkanias et al. ............. | 345/581 |
| 2009/0312998 | A1 * | 12/2009 | Berckmans et al. ............ | 703/11 |
| 2010/0030059 | A1 * | 2/2010 | Otte ............................... | 600/407 |
| 2010/0042011 | A1 * | 2/2010 | Doidge et al. ................ | 600/544 |
| 2010/0145202 | A1 * | 6/2010 | Mclaughlin et al. .......... | 600/509 |
| 2010/0191077 | A1 * | 7/2010 | O'Kane ........................ | 600/306 |

(Continued)

*Primary Examiner* — William Thomson
*Assistant Examiner* — Bobby Soriano
(74) *Attorney, Agent, or Firm* — Pearl Cohen Zedek Latzer Baratz LLP (57) ABSTRACT

A computerized veracity testing system including a subject observation subsystem operative to provide an output representing at least one characteristic of a subject, the subject observation subsystem including a hand engagement unit including at least one physiological parameter sensor and having a selectable immobilizer for selectably immobilizing at least a portion of a hand of the subject and an automatically operable computerized analysis subsystem responsive to the output of the subject observation subsystem for providing an indication relevant to veracity of the subject.

40 Claims, 12 Drawing Sheets

(56) References Cited

U.S. PATENT DOCUMENTS

| | | |
|---|---|---|
| 2010/0292568 A1* | 11/2010 | Droitcour et al. ............. 600/425 |
| 2011/0043759 A1* | 2/2011 | Bushinsky .................... 351/210 |
| 2011/0227737 A1* | 9/2011 | Kamins ...................... 340/573.1 |
| 2011/0260830 A1* | 10/2011 | Weising ....................... 340/5.52 |
| 2011/0288382 A1* | 11/2011 | Finburgh et al. .............. 600/301 |
| 2012/0004518 A1* | 1/2012 | D'Souza et al. .............. 600/301 |
| 2012/0022343 A1* | 1/2012 | Shastri et al. ................. 600/306 |
| 2012/0195473 A1* | 8/2012 | De Haan et al. .............. 382/107 |
| 2012/0310107 A1* | 12/2012 | Doidge et al. ................ 600/545 |
| 2013/0077823 A1* | 3/2013 | Mestha et al. ................ 382/103 |
| 2013/0225950 A1* | 8/2013 | Van Elswijk et al. ......... 600/309 |

* cited by examiner

POLYGRAPH

FIELD OF THE INVENTION

The present invention relates generally to veracity testing.

BACKGROUND OF THE INVENTION

The following publications are considered to represent the current state of the art: U.S. Pat. Nos. 7,972,140; 7,967,750 7,831,061; 7,822,783; 7,431,700; 6,873,716; 6,339,715; 6,062,216; 5,892,575; 5,792,049; 5,507,291; 5,467,122; 5,278,403; 5,241,360; 5,142,372; 4,289,142; 4,123,160; 4,085,740; 3,230,951; 2,944,542; re: 33,865, U.S. Published Patent Application 2004/0031906 and Published PCT Patent Applications: WO/2010/104480; WO/2010/092366; and WO/2008/029121.

SUMMARY OF THE INVENTION

The present invention seeks to provide improved systems for veracity testing.

There is thus provided in accordance with a preferred embodiment of the present invention a computerized veracity testing system including a subject observation subsystem operative to provide an output representing at least one characteristic of a subject, the subject observation subsystem including a hand engagement unit including at least one physiological parameter sensor and having a selectable immobilizer for selectably immobilizing at least a portion of a hand of the subject and an automatically operable computerized analysis subsystem responsive to the output of the subject observation subsystem for providing an indication relevant to veracity of the subject.

Preferably, the subject observation subsystem also includes a selectable arm immobilizer for selectably immobilizing an arm of the subject.

In accordance with a preferred embodiment of the present invention the subject observation subsystem also includes a motion detector for sensing breathing.

Preferably, the subject observation subsystem includes multiple detectors for sensing breathing and analysis circuitry operative to use outputs from the multiple detectors for providing an enhanced reliability indication of changes in breathing rate. Additionally, the multiple detectors for sensing breathing include at least one camera.

Preferably, the subject observation subsystem includes multiple detectors for sensing heart rate and analysis circuitry operative to use outputs from the multiple detectors for providing an enhanced reliability indication of changes in heart rate. Additionally, the multiple detectors for sensing heart rate include at least one camera.

In accordance with a preferred embodiment of the present invention the hand engagement unit of the subject observation subsystem includes multiple detection circuits for sensing skin conductivity and analysis circuitry operative to use outputs from the multiple detection circuits for providing an enhanced reliability indication of changes in skin conductivity.

There is also provided in accordance with another preferred embodiment of the present invention a computerized veracity testing system including a multiplicity of subject observation subsystems, each of which is operative to provide an output and a central automatically operable computerized analysis subsystem, remote from the multiplicity of subject observation subsystems, the central automatically operable computerized analysis subsystem being operative to provide an indication relevant to veracity of the subject at least in near real time.

Preferably, at least one of the multiplicity of subject observation subsystems is operative to provide an output representing at least one visually sensible characteristic of a subject and the subject observation subsystem includes a hand engagement unit including at least one physiological parameter sensor and having a selectable immobilizer for selectably immobilizing at least a portion of a hand of the subject.

In accordance with a preferred embodiment of the present invention at least one of the multiplicity of subject observation subsystems includes multiple detectors for sensing heart rate and analysis circuitry operative to use outputs from the multiple detectors for providing an enhanced reliability indication of changes in heart rate. Additionally, at least one of the multiple detectors is a camera.

Preferably, the hand engagement unit includes multiple detection circuits for sensing skin conductivity and analysis circuitry operative to use outputs from the multiple detection circuits for providing an enhanced reliability indication of changes in skin conductivity.

In accordance with a preferred embodiment of the present invention at least one of the multiplicity of subject observation subsystems also includes a selectable arm immobilizer for selectably immobilizing an arm of the subject. Additionally or alternatively, at least one of the multiplicity of subject observation subsystems also includes a motion detector for sensing breathing.

Preferably, at least one of the multiplicity of subject observation subsystems includes multiple detectors, at least one of which is a camera, for sensing breathing and analysis circuitry operative to use outputs from the multiple detectors for providing an enhanced reliability indication of changes in breathing rate.

There is further provided in accordance with yet another preferred embodiment of the present invention a computerized veracity testing system including a subject observation subsystem operative to provide an output representing at least one characteristic of a subject, the subject observation subsystem including a motion detector providing an output which is employed for ascertaining breathing rate.

There is yet further provided in accordance with still another preferred embodiment of the present invention a computerized veracity testing system including a subject observation subsystem operative to provide an output representing at least one characteristic of a subject, the subject observation subsystem including multiple different types of sensors providing outputs useful for ascertaining at least one of heart rate; breathing rate and skin conductivity and an automatically operable computerized analysis subsystem responsive to the output of the subject observation subsystem for providing an indication relevant to veracity of the subject.

Preferably, the multiple different types of sensors include at least one of a thermal camera and a motion detector, outputs of both of which are employed to ascertain breathing rate, a PPG sensor and a thermal camera, outputs of both of which are employed to ascertain heart rate and which may be also used to calculate breathing rate and one or more EDA sensors and a motion detector, outputs of both of which are employed to ascertain skin conductivity.

BRIEF DESCRIPTION OF THE DRAWINGS

The present invention will be understood and appreciated more fully with reference to the drawings in which.

DETAILED DESCRIPTION OF PREFERRED EMBODIMENTS

Figure 1:
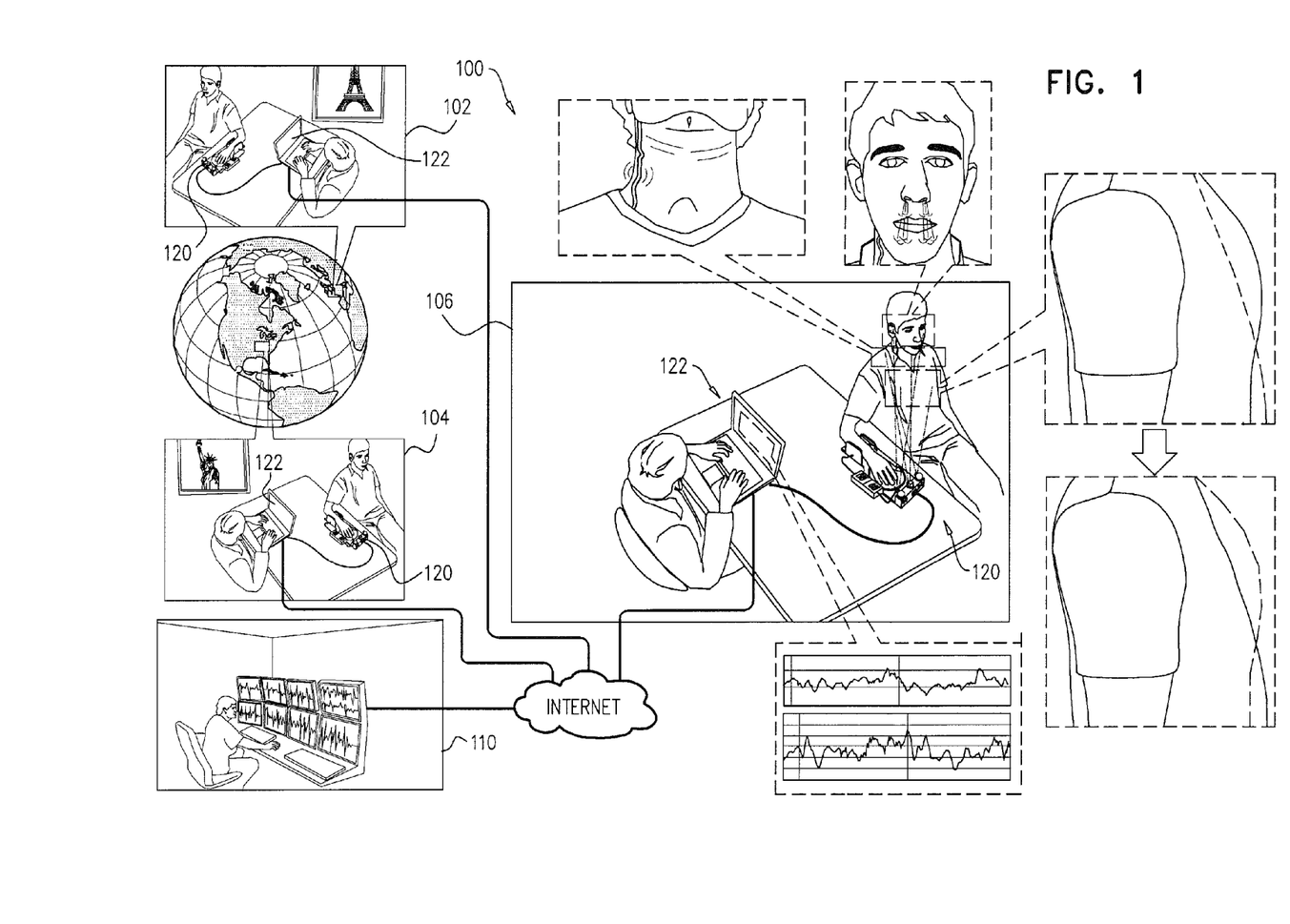
FIG. 1 is a simplified pictorial illustration of a distributed computerized veracity testing system constructed and operative in accordance with a preferred embodiment of the present invention.

Reference is now made to FIG. 1, which is a simplified pictorial illustration of a distributed computerized veracity testing system constructed and operative in accordance with a preferred embodiment of the present invention.

As seen in FIG. 1, there is provided a computerized veracity testing system generally designated by reference numeral 100. In the illustrated embodiment, the computerized veracity testing system 100 is a distributed system and includes a plurality of veracity testing sites, here designated by reference numerals 102, 104 and 106, which may be interconnected with a veracity analysis center 110, which may be remote from all or some of the veracity testing sites. The various veracity testing sites may communicate unidirectionally or bidirectionally via any suitable data network, such as the internet.

It is appreciated that features described hereinbelow may also be applicable to a non-distributed veracity testing system wherein a single veracity testing site is co-located with veracity analysis functionality.

In accordance with a preferred embodiment of the present invention, at each veracity testing site there is provided a subject observation subsystem including a subject observation assembly, generally designated by reference numeral 120, operative to provide an output representing at least one characteristic of a subject and a data receiving computer 122.

Further in accordance with a preferred embodiment of the present invention there is provided veracity analysis functionality, which may be, as mentioned above, at a discrete veracity analysis site, such as a veracity analysis center 110, or co-located with a subject observation subsystem, and preferably embodied in a data receiving computer 122.

Figure 2A:
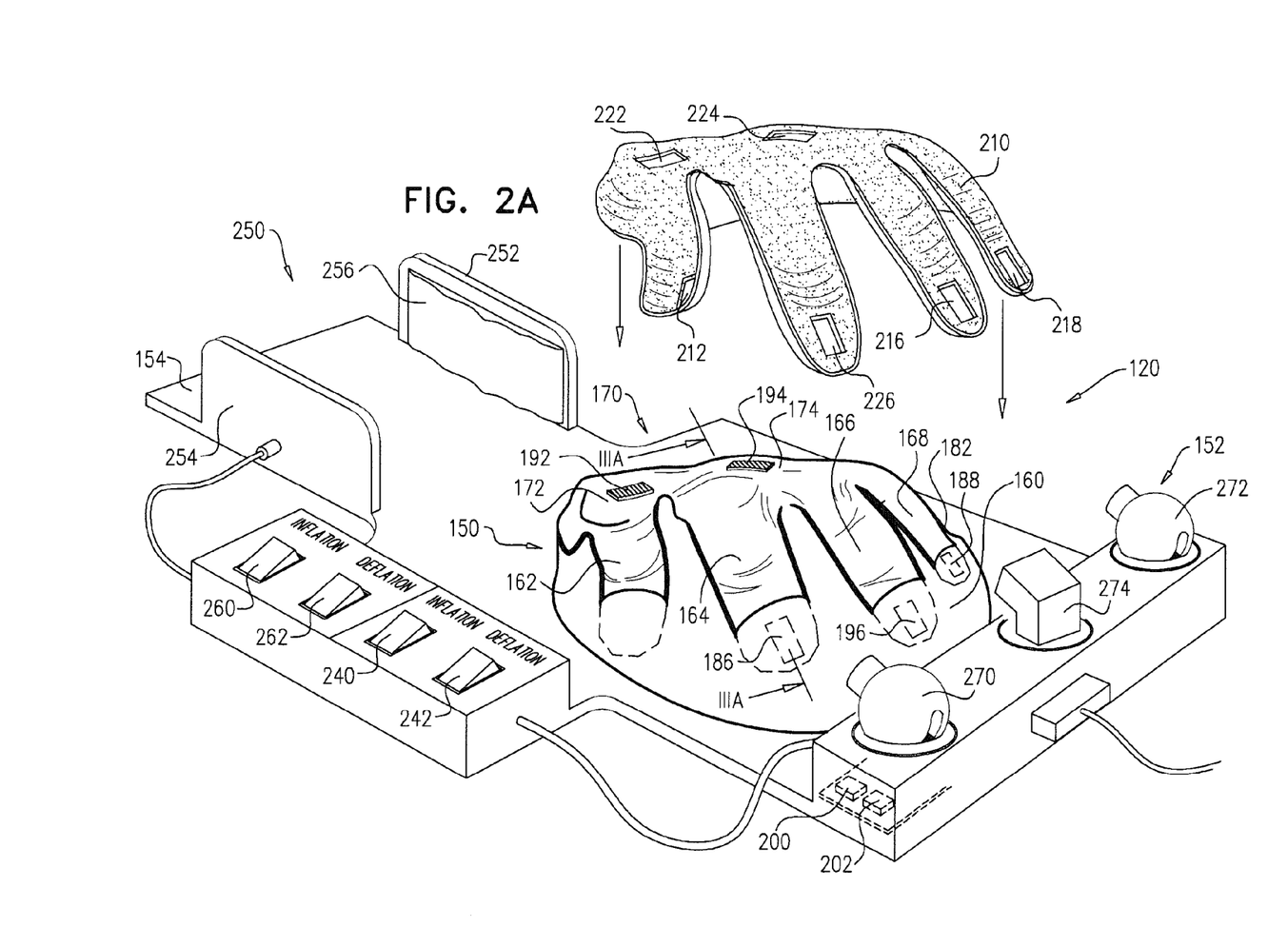
FIGS. 2A & 2B are simplified respective exploded view and assembled view pictorial illustrations of a subject observation subsystem forming part of a computerized veracity testing system constructed and operative in accordance with a preferred embodiment of the present invention.
Figure 2B:
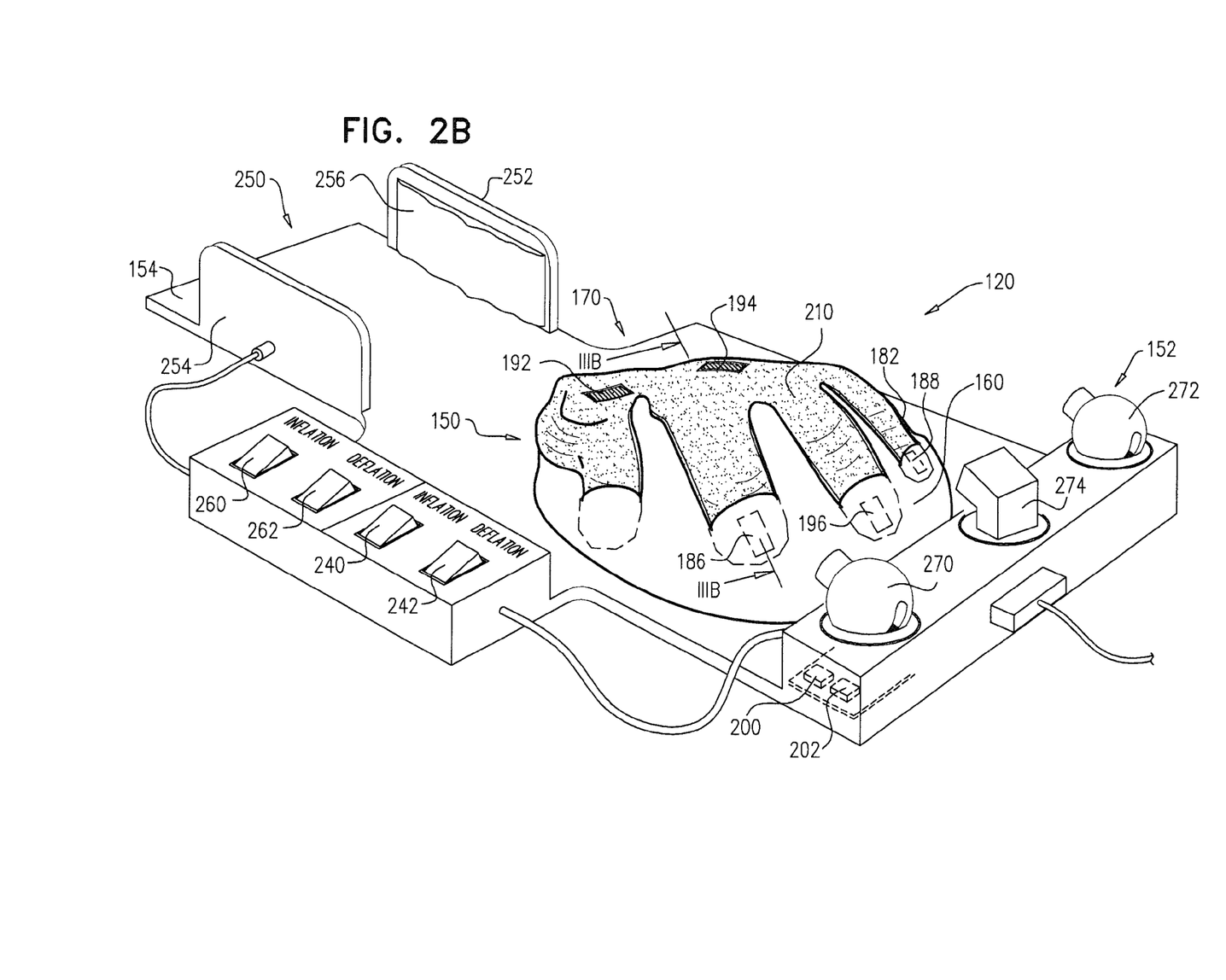
Figure 2C:
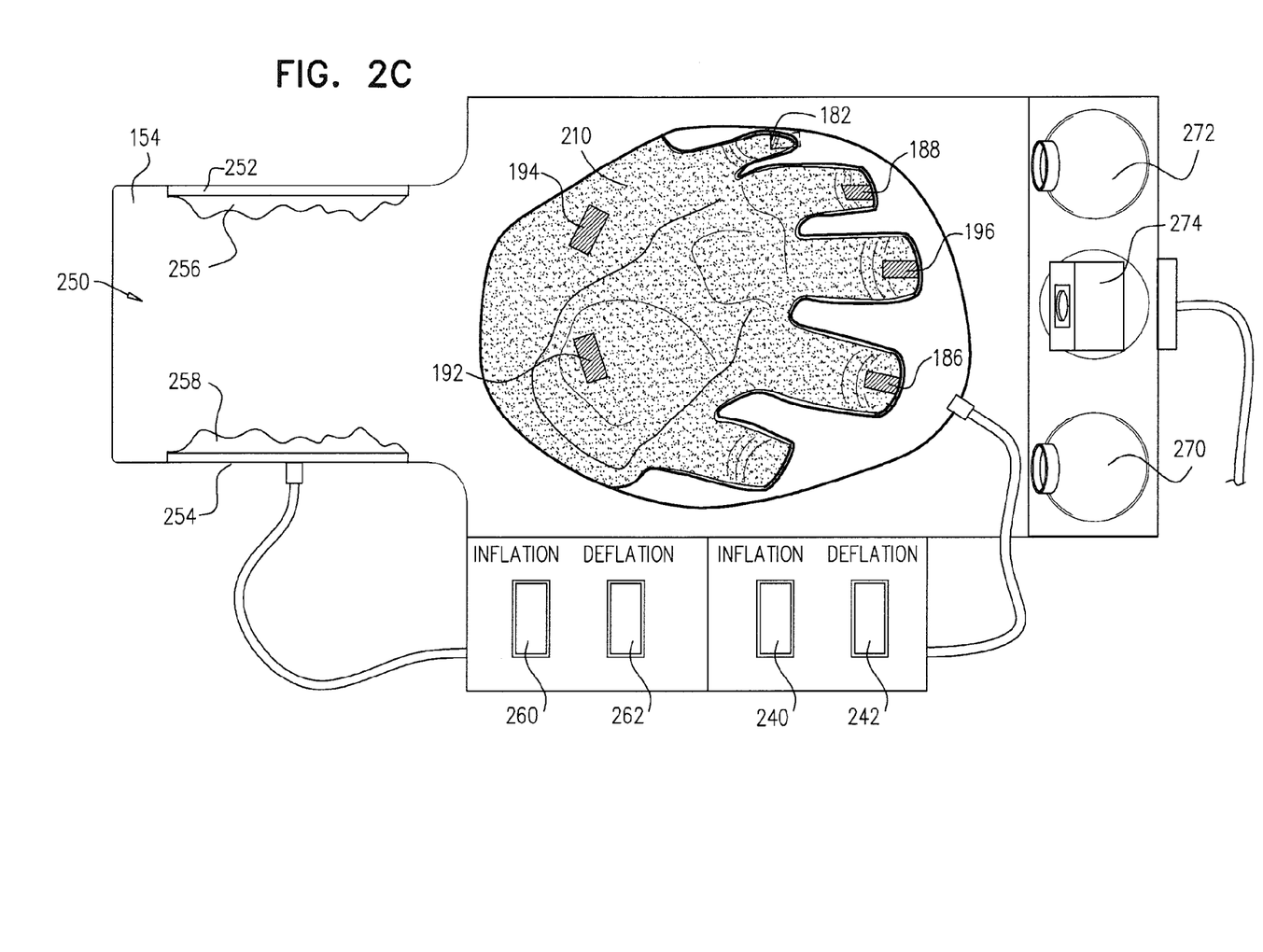
FIG. 2C is a simplified top view illustration of a subject observation subsystem of FIGS. 2A & 2B.
Figure 2D:
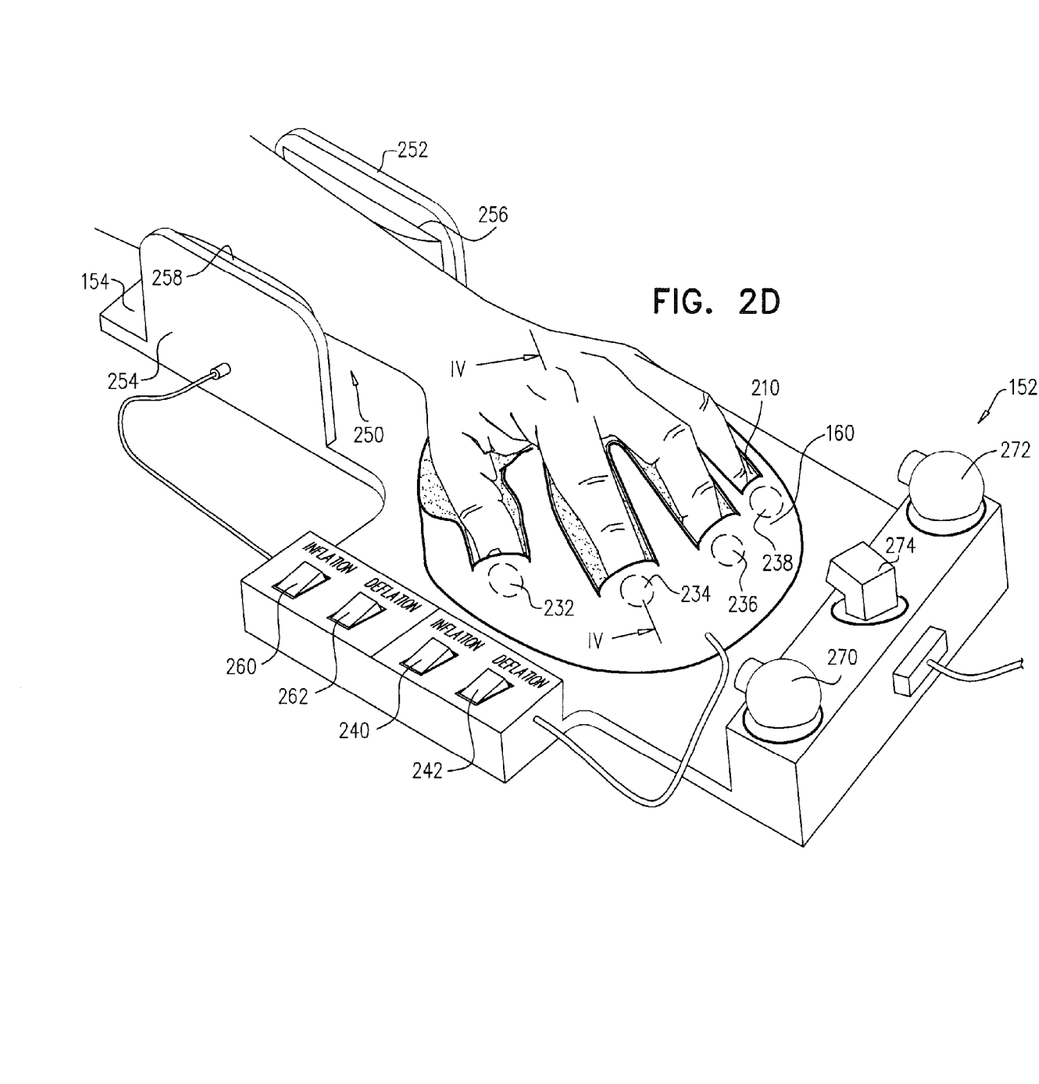
FIG. 2D is a simplified illustration of hand engagement with the subject observation subsystem of FIGS. 2A-2C.
Figure 3A:
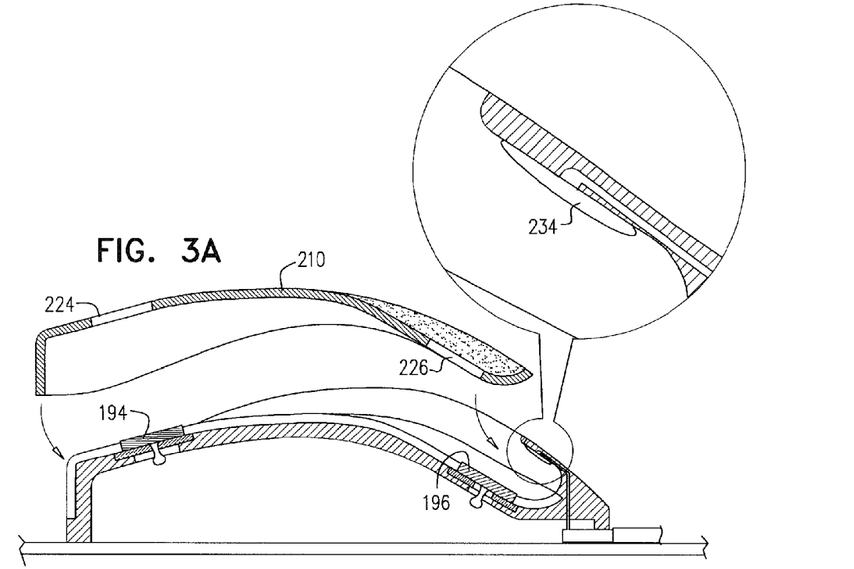
FIGS. 3A & 3B are simplified sectional illustrations, taken along respective lines IIIA-IIIA and IIIB-IIIB of corresponding FIGS. 2A & 2B.
Figure 3B:
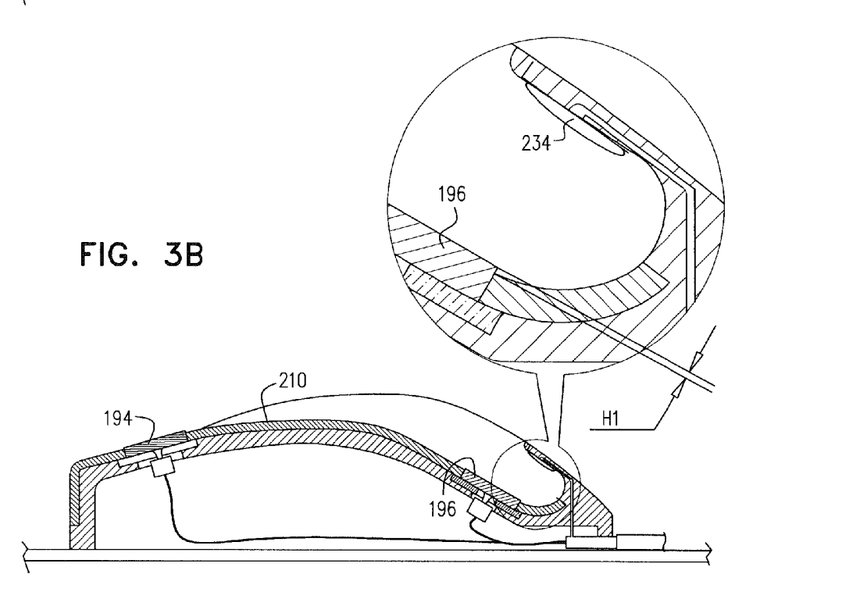
Figure 4A:
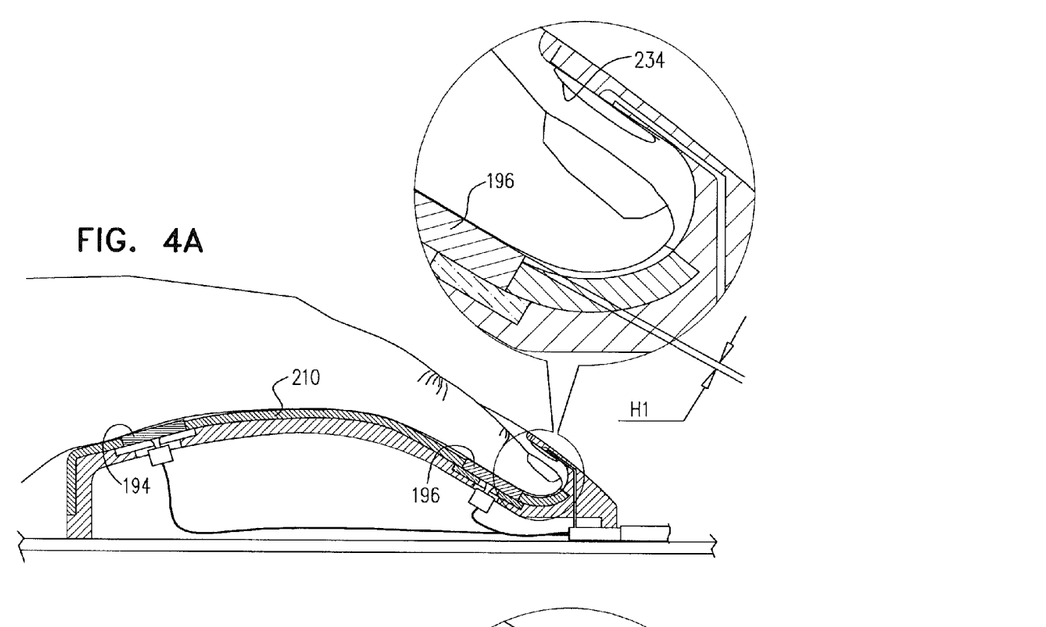
FIGS. 4A & 4B are simplified sectional illustrations taken along lines IV-IV in FIG. 2D in respective non-immobilized and immobilized operative orientations.
Figure 4B:
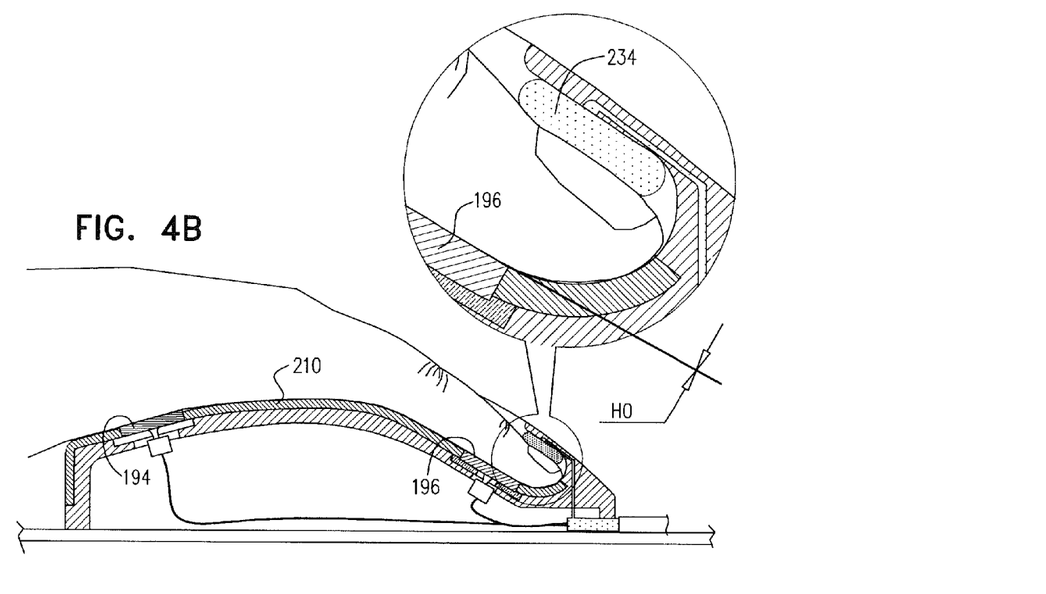

Reference is now made additionally to FIGS. 2A & 2B, which are simplified respective exploded view and assembled view pictorial illustrations of a subject observation subsystem forming part of a computerized veracity testing system constructed and operative in accordance with a preferred embodiment of the present invention, to FIG. 2C, which is a simplified top view illustration of a subject observation subsystem of FIGS. 2A & 2B, to FIG. 2D, which is a simplified illustration of hand engagement with the subject observation subsystem of FIGS. 2A-2C, to FIGS. 3A & 3B, which are simplified sectional illustrations, taken along respective lines IIIA-IIIA and IIIB-IIIB of corresponding FIGS. 2A & 2B, and to FIGS. 4A & 4B, which are simplified sectional illustrations taken along lines IV-IV in FIG. 2D, in respective non-immobilized and immobilized operative orientations.

As seen in FIGS. 1-4B, the subject observation subsystem 120 includes a hand engagement unit 150 and a camera assembly 152, both of which are preferably mounted on a common base 154.

The hand engagement unit 150 preferably comprises an ergonomically shaped hand rest base element 160, which is fixedly mounted onto common base 154. Hand rest base element 160 preferably includes four finger support areas 162, 164, 166 and 168 and a palm support area 170 including first and second palm support regions 172 and 174.

A plurality of physiological sensor contacts are preferably replaceably mounted in base element 160 for engagement with a subject's hand when it is supported at support areas 162, 166, 168, 172 and 174.

In accordance with a preferred embodiment of the present invention, electro-dermal activity (EDA) sensor contacts 182, 186, 188, 192 & 194, each preferably a 030340 EDA Sensor Contact, commercially available from Mindlife Solutions Ltd, Jerusalem Technological Park, Bldg. 1/C, Jerusalem, 96951 Israel, are located at respective support areas 162, 166, 168, 172 and 174.

In accordance with a preferred embodiment of the present invention, a photoplethysmograph (PPG) sensor contact 196, preferably a 6010-F, commercially available from HeartMath LLC, 14700 West Park Ave, Boulder Creek, Calif. 95006 USA, is located at support area 164.

One or more EDA processing circuit 200 receives outputs from sensor contacts 182, 186, 188, 192 & 194. Preferably the EDA processing circuit is a 030300 EDA, commercially available from Mindlife Solutions Ltd, Jerusalem Technological Park, Bldg. 1/C, Jerusalem, 96951 Israel.

A PPG processing circuit 202 receives outputs from sensor contact 196. Preferably the PPG processing circuit is a 6010-M, commercially available from HeartMath LLC, 14700 West Park Ave, Boulder Creek, Calif. 95006 USA.

Preferably sweat wicking hand contact surface layer 210 is provided over base element 160 and is formed with apertures 212, 216, 218, 222, 224 & 226, for accommodating contacts 182, 186, 188, 192, 194 & 196.

As seen particularly in FIGS. 2D-4B, selectably inflatable finger immobilization elements 232, 234, 236 and 238 are mounted generally as shown facing respective support areas 162, 164, 166, 168 for immobilizing a subject's fingers when his hand in operative engagement with the hand engagement unit 150. FIGS. 4A and 4B show respective non-inflated and inflated states of one of the selectably inflatable elements 232-238.

Inflation and deflation controls 240 and 242 are preferably provided for enabling an operator to control inflation of selectably inflatable finger immobilization elements 232, 234, 236 and 238.

Further in accordance with a preferred embodiment of the invention, there is provided a selectable arm immobilizer 250 for selectably immobilizing an arm of said subject. Selectable arm immobilizer 250 preferably comprises a pair of upstanding plates 252 and 254, which are fixedly mounted onto common base 154. A pair of selectably inflatable arm immobilization elements 256 and 258 are mounted on inner facing surfaces of plates 252 and 254.

Inflation and deflation controls 260 and 262 are preferably provided for enabling an operator to control inflation of selectably inflatable arm immobilization elements 256 and 258.

Camera assembly 152 preferably comprises first and second thermal imaging cameras 270 and 272 which are preferably arranged to view the mouth and nose of the subject and the side neck region of the subject, respectively. Camera assembly 152 also comprises a motion detector 274. A preferred motion detector 274 is a cn 8537022606, commercially available from Prime Sense, 28 Habarzel St. Tel-Aviv 69710 Israel. The motion detector 274 preferably views the chest of the subject.

It is a particular feature of a preferred embodiment of the present invention that breathing rate is ascertained by use of a motion detector.

It is a further particular feature of a preferred embodiment of the present invention that at least one of heart rate, breathing rate and skin conductivity is ascertained by use of multiple different types of detectors. Examples of multiple different types of detectors which may be used for this purpose include:
- a thermal camera and a motion detector, outputs of both of which are employed to ascertain breathing rate;
- a PPG sensor and a thermal camera, outputs of both of which are employed to ascertain heart rate and which may be also used to calculate breathing rate; and
- one or more EDA sensors and a motion detector, outputs of both of which are employed to ascertain skin conductivity.

Figure 5:
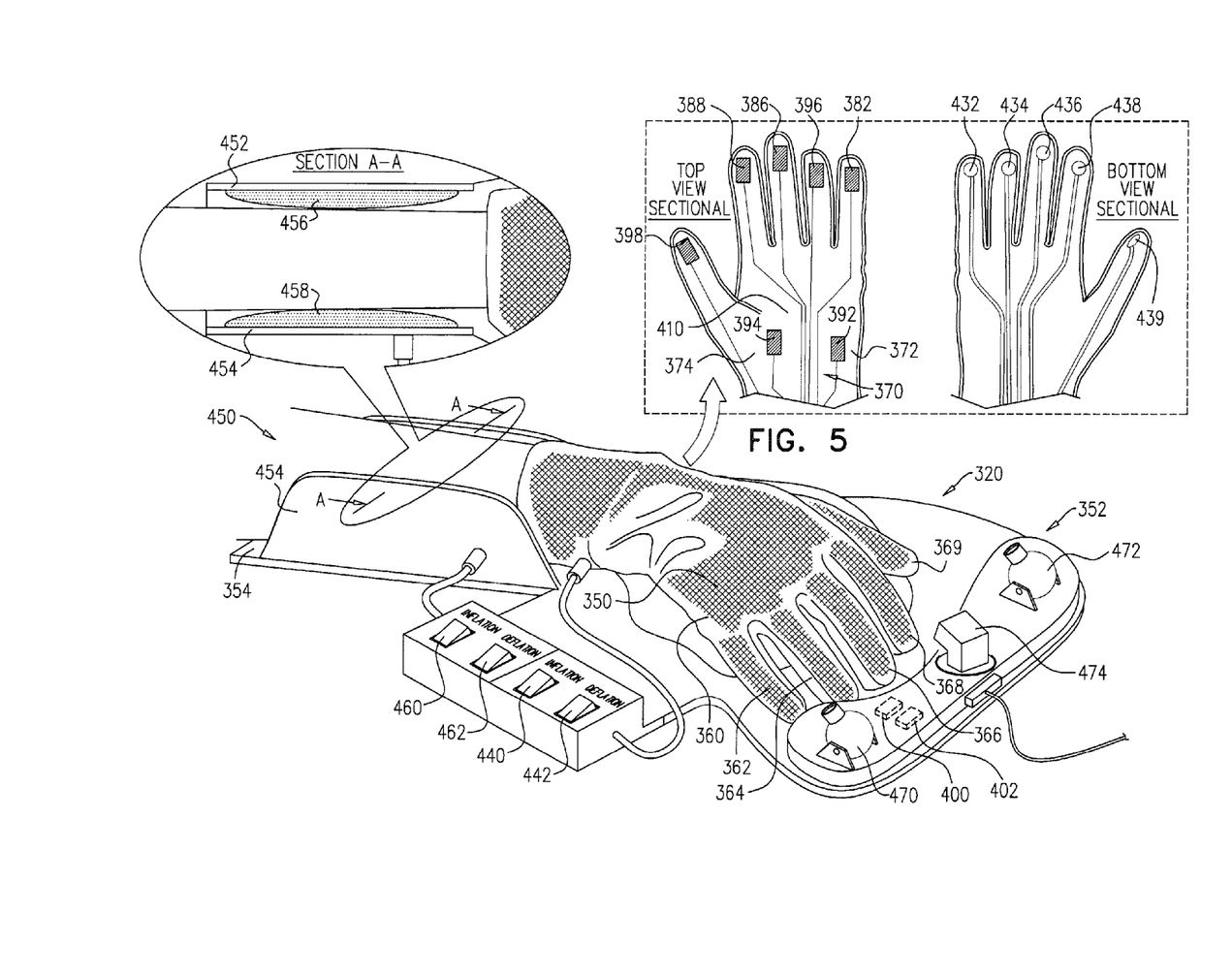
FIG. 5 is a simplified illustration of an alternative embodiment of a subject observation subsystem, forming part of a computerized veracity testing system constructed and operative in accordance with a preferred embodiment of the present invention.

Reference is now made to FIG. 5, which is a simplified pictorial illustration of a subject observation subsystem 320, forming part of a computerized veracity testing system constructed and operative in accordance with another preferred embodiment of the present invention.

As seen in FIG. 5, the subject observation subsystem 320 includes a hand engagement unit 350 and a camera assembly 352, both of which are preferably mounted on a common base 354.

The hand engagement unit 350 preferably comprises a glove element 360, which is mounted onto common base 354. Glove element 360 preferably includes five finger engagement areas 362, 364, 366, 368 and 369 and a palm engagement area 370 including first and second palm support regions 372 and 374.

A plurality of physiological sensor contacts are preferably mounted in glove element 360 for engagement with a subject's hand when it is fully inserted into glove element 360.

In accordance with a preferred embodiment of the present invention, electro-dermal activity (EDA) sensor contacts 382, 386, 388, 392 & 394 each preferably a 030340 EDA Sensor Contact, commercially available from Mindlife Solutions Ltd, Jerusalem Technological Park, Bldg. 1/C, Jerusalem, 96951 Israel, are located at respective engagement areas 362, 366, 368, 372 and 374.

In accordance with a preferred embodiment of the present invention, a photoplethysmograph (PPG) sensor contact 396, preferably a 6010-F, commercially available from HeartMath LLC, 14700 West Park Ave, Boulder Creek, Calif. 95006 USA, is located at engagement area 364.

Further in accordance with a preferred embodiment of the present invention at least one additional sensor 398, such as a temperature sensor, is located at engagement area 369.

One or more EDA processing circuit 400 receives outputs from sensor contacts 382, 386, 388, 392 & 394. Preferably the EDA processing circuit is a 030300 EDA, commercially available from Mindlife Solutions Ltd, Jerusalem Technological Park, Bldg. 1/C, Jerusalem, 96951 Israel.

A PPG processing circuit 402 receives outputs from sensor contact 396. Preferably the PPG processing circuit is a 6010-M, commercially available from HeartMath LLC, 14700 West Park Ave, Boulder Creek, Calif. 95006 USA.

Preferably glove element 360 includes a sweat wicking hand contact surface layer 410.

Selectably inflatable finger immobilization elements 432, 434, 436, 438 and 439 are mounted generally as shown facing respective engagement areas 362, 364, 366, 368 and 369 for immobilizing a subject's fingers when his hand in operative engagement with the hand engagement unit 350.

Inflation and deflation controls 440 and 442 are preferably provided for enabling an operator to control inflation of selectably inflatable finger immobilization elements 432, 434, 436, 438 and 439.

Further in accordance with a preferred embodiment of the invention, there is provided a selectable arm immobilizer 450 for selectably immobilizing an arm of said subject. Selectable arm immobilizer 450 preferably comprises a pair of upstanding plates 452 and 454, which are fixedly mounted onto common base 354. A pair of selectably inflatable arm immobilization elements 456 and 458 are mounted on inner facing surfaces of plates 452 and 454.

Inflation and deflation controls 460 and 462 are preferably provided for enabling an operator to control inflation of selectably inflatable arm immobilization elements 456 and 458.

Camera assembly 352 preferably comprises first and second thermal imaging cameras 470 and 472 which are preferably arranged to view the mouth and nose of the subject and the side neck region of the subject, respectively. Camera assembly 352 also comprises a motion detector 474. A preferred motion detector 474 is a en 8537022606, commercially available from Prime Sense, 28 Habarzel St., Tel-Aviv 69710 Israel. The motion detector 474 preferably views the chest of the subject.

Figure 6A:
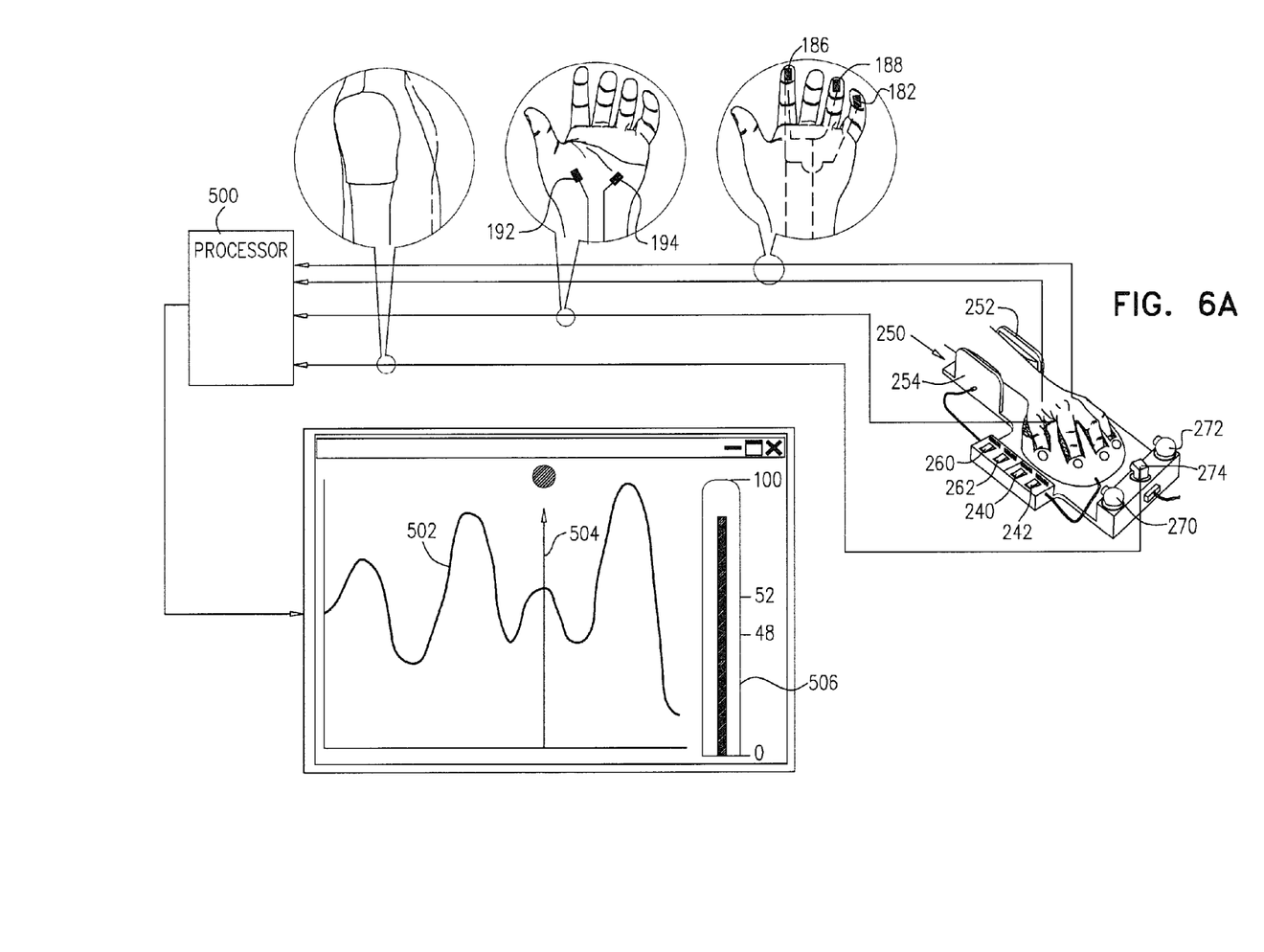
FIGS. 6A, 6B and 6C are simplified illustrations of three different output functionalities employing multiple different types of sensors, preferably provided by the veracity testing system of a preferred embodiment of the present invention.
Figure 6B:
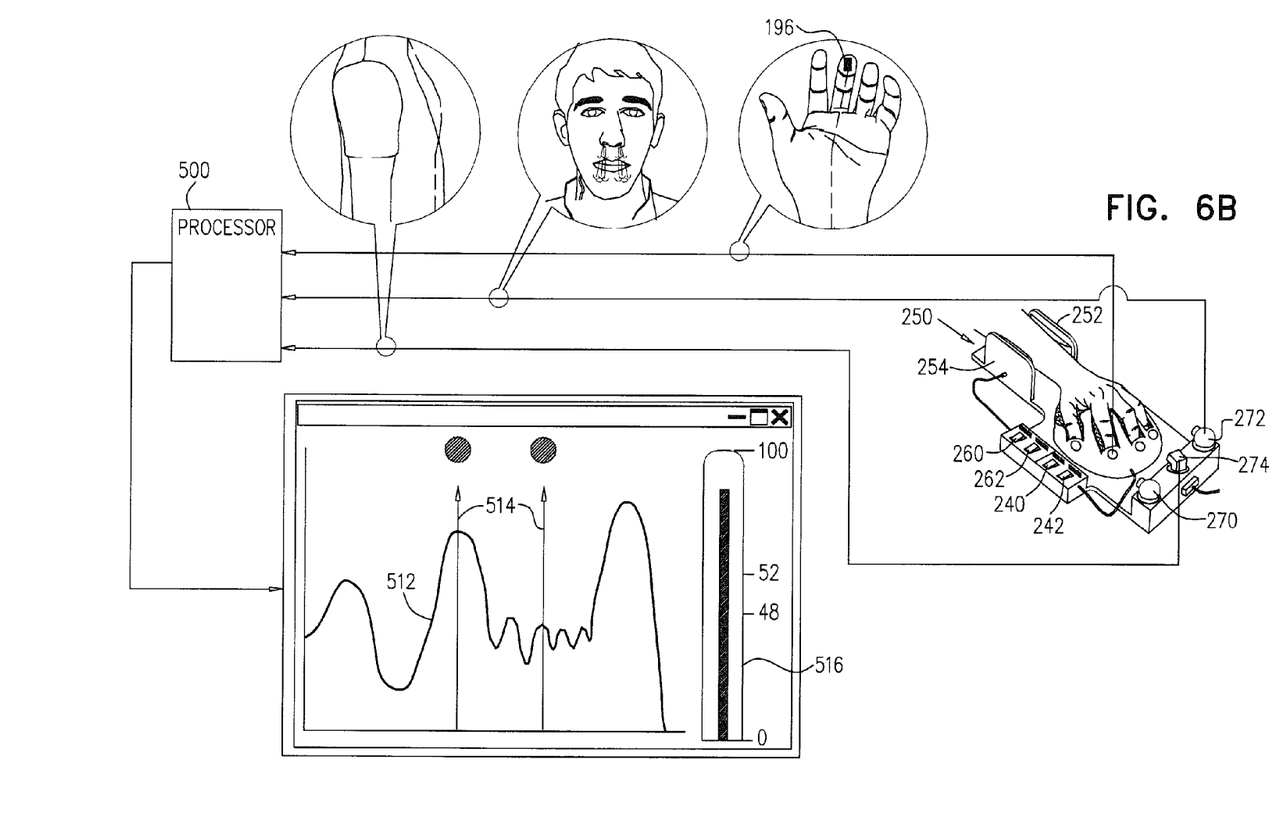
Figure 6C:
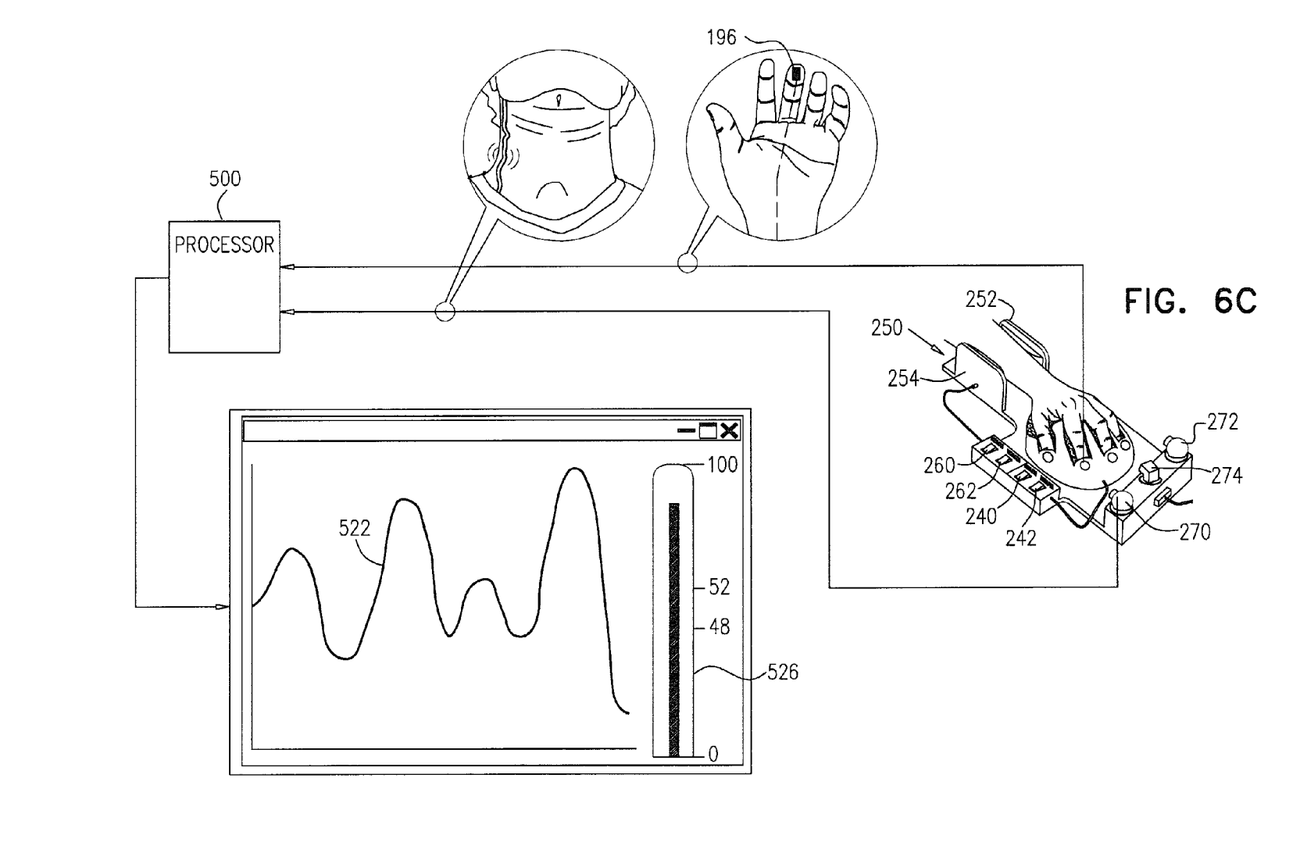

Reference is now made to FIGS. 6A, 6B and 6C, which are simplified illustrations of three different output functionalities employing multiple different types of sensors, preferably provided by the veracity testing system of a preferred embodiment of the present invention.

As noted above, it is a particular feature of the present invention that the subject observation subsystem of the present invention includes multiple different types of sensors providing outputs useful for ascertaining at least one of heart rate; breathing rate and skin conductivity and that there is provided an automatically operable computerized analysis subsystem responsive to said output of the subject observation subsystem for providing an indication relevant to veracity of the subject.

FIG. 6A illustrates a feature of the present invention wherein outputs from EDA finger sensors 182, 186 and 188 via multiple detection circuits, from EDA palm sensors 192 and 194 and from motion detector 274 are supplied to a processor 500, which may include processing circuits 200 and 202 (FIGS. 2A & 2B) or processing circuits 400 and 402 (FIG. 5). Processor 500 is operative to provide a skin conductivity change output 502, which typically appears on computer 122 (FIG. 1). In addition to the features described above, a particular feature of the conductivity change output 502 is the provision of one or more visual indications, here appearing as an arrow 504, which represents a sudden substantial chest movement of the subject, which is sensed by motion detector 274. In addition to the skin conductivity change output 502 there is preferably also provided a multi-parameter veracity indicator 506, which indicates the veracity of the subject based on the inputs provided to processor 500.

FIG. 6B illustrates a feature of the present invention wherein outputs from PPG sensor 196, from thermal camera 272 and from motion detector 274 are supplied to processor 500. Processor 500 is operative to provide a breathing rate change output 512, which typically appears on computer 122 (FIG. 1). In addition to the features described above, a particular feature of the breathing rate output 512 is the provision of one or more visual indications, here appearing as an arrow 514, which represents a sudden substantial chest movement of the subject, which is sensed by motion detector 274. In addition to the breathing rate change output 502 there is preferably also provided a multi-parameter veracity indicator 516, which indicates the veracity of the subject based on the inputs provided to processor 500.

FIG. 6C illustrates a feature of the present invention wherein outputs from PPG sensor 196 and from thermal camera 270 are supplied to processor 500. Processor 500 is operative to provide a heart rate change output 522, which typically appears on computer 122 (FIG. 1). In addition to the heart rate change output 522 there is preferably also provided a multi-parameter veracity indicator 526, which indicates the veracity of the subject based on the inputs provided to processor 500.

Figure 7:
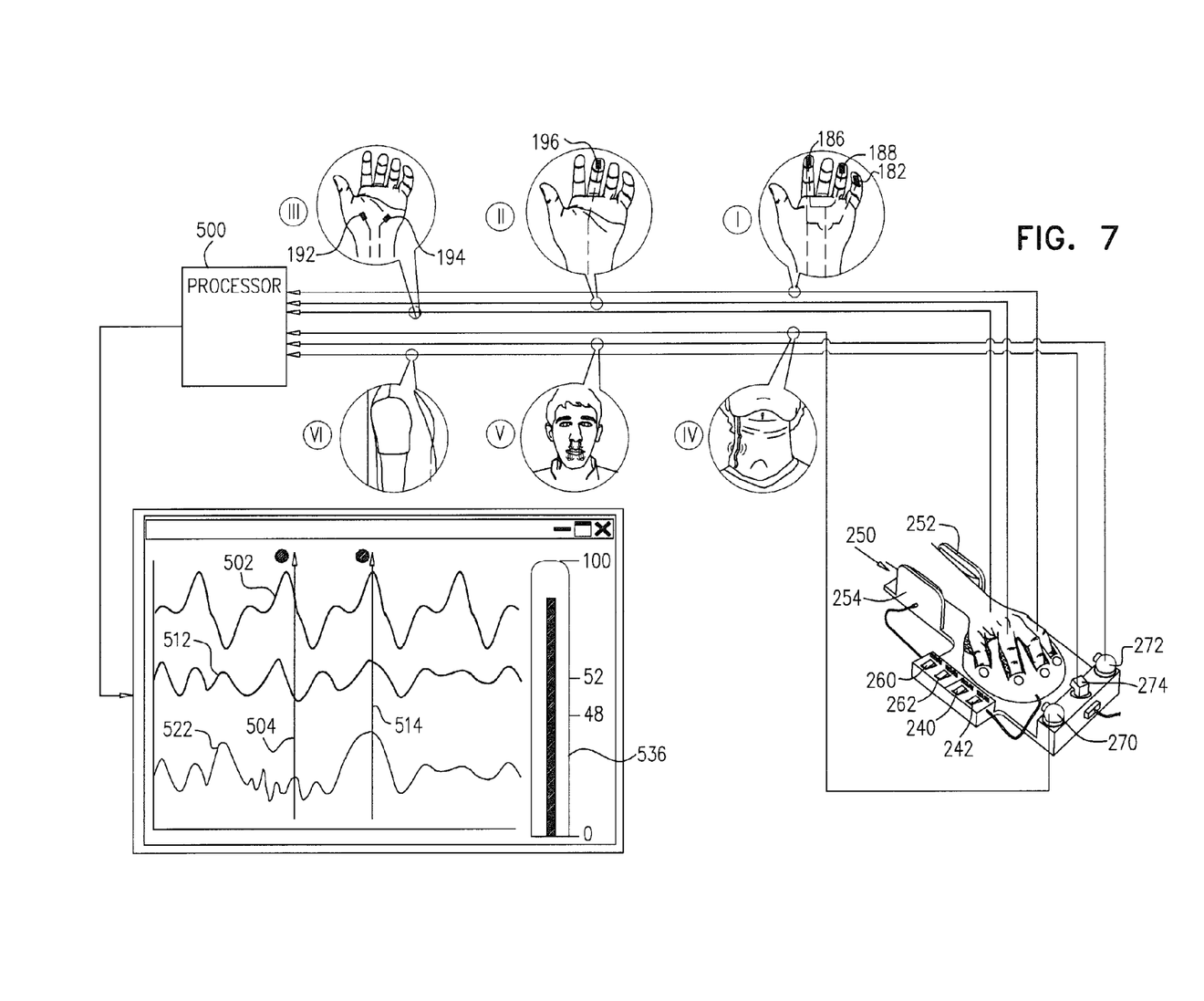
FIG. 7 is a simplified illustration of the operation of a veracity testing system providing the functionalities illustrated in FIGS. 6A, 6B and 6C.

Reference is now made to FIG. 7, which is a simplified illustration of the operation of a veracity testing system providing the functionalities illustrated in FIGS. 6A, 6B and 6C. As seen in FIG. 7, in a preferred embodiment of the present invention, the following outputs are preferably provided to processor 500:

I. a first EDA detection circuit output from EDA finger sensors 182, 186 and 188;

II. a PPG detection circuit output from PPG finger sensor 196;

III. a second EDA detection circuit output from EDA palm sensors 192 and 194;

IV. an output from thermal camera 270 viewing the subject's neck;

V. an output from thermal camera 272 viewing the subject's face; and

VI. an output from motion detector 274 viewing the subject's chest.

Processor 500 is operative to provide a skin conductivity change output 502, a breathing rate change output 512 and a heart rate change output 522, which typically appear on computer 122 (FIG. 1). In addition to the various features described above, a particular feature of this embodiment of the invention is the provision of one or more visual indications, here appearing as arrows 504 and 514, which represent sudden substantial chest movements of the subject, which is sensed by motion detector 274. In addition to the outputs 502, 512 and 522, there is preferably also provided a multi-parameter veracity indicator 536, which indicates the veracity of the subject based on the various inputs provided to processor 500.

It is appreciated that processor 500 may also include additional processing circuits receiving outputs from the at least one additional sensor 398 (FIG. 5).

It is also appreciated that hand engagement units 150 and 350 may be configured for engagement with either the left hand or the right hand of the subject under observation.

It will be appreciated by persons skilled in the art that the present invention is not limited by what has been particularly shown and described hereinabove. The scope of the present invention also includes combinations and subcombinations of various features described hereinabove as well as variations and modifications thereof which would occur to persons skilled in the art upon reading the foregoing description and are not in the prior art.

The invention claimed is:

1. A computerized veracity testing system comprising:
a subject observation subsystem operative to provide an output representing at least one characteristic of a subject, said subject observation subsystem comprising:
at least one physiological parameter sensor; and
a hand engagement unit comprising:
a base element having separated finger support areas, each support area to support one finger of the subject;
a plurality of physiological sensor contacts mounted in said finger support areas;
selectably inflatable finger immobilization elements, each facing a respective finger support area for immobilizing a subject's fingers when his hand in operative engagement with the engagement unit; and
an automatically operable computerized analysis subsystem responsive to said output of said subject observation subsystem for providing an indication relevant to veracity of the subject.

2. A computerized veracity testing system according to claim 1 and wherein said subject observation subsystem also comprises a selectable arm immobilizer for selectably immobilizing an arm of said subject.

3. A computerized veracity testing system according to claim 1 and wherein said subject observation subsystem also comprises a motion detector for sensing breathing.

4. A computerized veracity testing system according to claim 3 and wherein said subject observation subsystem comprises:
multiple detectors for sensing breathing; and
analysis circuitry operative to use outputs from said multiple detectors for providing an enhanced reliability indication of changes in breathing rate.

5. A computerized veracity testing system according to claim 4 and wherein said hand engagement unit of said subject observation subsystem comprises:
multiple detection circuits for sensing skin conductivity; and
analysis circuitry operative to use outputs from said multiple detection circuits for providing an enhanced reliability indication of changes in skin conductivity.

6. A computerized veracity testing system according to claim 4 and wherein said subject observation subsystem comprises:
multiple detectors, at least one of which is a camera, for sensing heart rate; and
analysis circuitry operative to use outputs from said multiple detectors for providing an enhanced reliability indication of changes in heart rate.

7. A computerized veracity testing system according to claim 6 and wherein said hand engagement unit of said subject observation subsystem comprises:
multiple detection circuits for sensing skin conductivity; and analysis circuitry operative to use outputs from said multiple detection circuits for providing an enhanced reliability indication of changes in skin conductivity.

8. A computerized veracity testing system according to claim 7 and wherein said subject observation subsystem also comprises a selectable arm immobilizer for selectably immobilizing an arm of said subject.

9. A computerized veracity testing system according to claim 3 and wherein said subject observation subsystem comprises:
multiple detectors, at least one of which is a camera, for sensing heart rate; and
analysis circuitry operative to use outputs from said multiple detectors for providing an enhanced reliability indication of changes in heart rate.

10. A computerized veracity testing system according to claim 9 and wherein said hand engagement unit of said subject observation subsystem comprises:
multiple detection circuits for sensing skin conductivity; and
analysis circuitry operative to use outputs from said multiple detection circuits for providing an enhanced reliability indication of changes in skin conductivity.

11. A computerized veracity testing system according to claim 10 and wherein said subject observation subsystem also comprises a selectable arm immobilizer for selectably immobilizing an arm of said subject.

12. A computerized veracity testing system according to claim 1 and wherein said subject observation subsystem comprises:
multiple detectors, at least one of which is a camera, for sensing breathing; and
analysis circuitry operative to use outputs from said multiple detectors for providing an enhanced reliability indication of changes in breathing rate.

13. A computerized veracity testing system according to claim 12 and wherein said subject observation subsystem comprises:
multiple detectors for sensing heart rate; and
analysis circuitry operative to use outputs from said multiple detectors for providing an enhanced reliability indication of changes in heart rate.

14. A computerized veracity testing system according to claim 13 and wherein said hand engagement unit of said subject observation subsystem comprises:
multiple detection circuits for sensing skin conductivity; and
analysis circuitry operative to use outputs from said multiple detection circuits for providing an enhanced reliability indication of changes in skin conductivity.

15. A computerized veracity testing system according to claim 12 and wherein said hand engagement unit of said subject observation subsystem comprises:
multiple detection circuits for sensing skin conductivity; and
analysis circuitry operative to use outputs from said multiple detection circuits for providing an enhanced reliability indication of changes in skin conductivity.

16. A computerized veracity testing system according to claim 15 and wherein said subject observation subsystem also comprises a selectable arm immobilizer for selectably immobilizing an arm of said subject.

17. A computerized veracity testing system according to claim 1 and wherein said subject observation subsystem comprises:
multiple detectors, at least one of which is a camera, for sensing heart rate; and
analysis circuitry operative to use outputs from said multiple detectors for providing an enhanced reliability indication of changes in heart rate.

18. A computerized veracity testing system according to claim 17 and wherein said hand engagement unit of said subject observation subsystem comprises:
multiple detection circuits for sensing skin conductivity; and
analysis circuitry operative to use outputs from said multiple detection circuits for providing an enhanced reliability indication of changes in skin conductivity.

19. A computerized veracity testing system according to claim 18 and wherein said subject observation subsystem also comprises a selectable arm immobilizer for selectably immobilizing an arm of said subject.

20. A computerized veracity testing system according to claim 1 and wherein said hand engagement unit of said subject observation subsystem comprises:
multiple detection circuits for sensing skin conductivity; and
analysis circuitry operative to use outputs from said multiple detection circuits for providing an enhanced reliability indication of changes in skin conductivity.

21. A computerized veracity testing system according to claim 1, further comprising:
at least one additional subject observation subsystem operative to provide at least one additional output; and
wherein:
said automatically operable computerized analysis subsystem comprises a central automatically operable computerized analysis subsystem, remote from said subject observation subsystem and from said at least one additional subject observation subsystem, said central automatically operable computerized analysis subsystem being operative in response to said output and said at least one additional output to provide an indication relevant to veracity of the subject at least in near real time.

22. A computerized veracity testing system according to claim 21 and wherein:
at least one of said at least one additional subject observation subsystem is operative to provide an output representing at least one visually sensible characteristic of a subject.

23. A computerized veracity testing system according to claim 22 and wherein at least one of said at least one additional subject observation subsystem comprises:
multiple detectors, at least one of which is a camera, for sensing heart rate; and
analysis circuitry operative to use outputs from said multiple detectors for providing an enhanced reliability indication of changes in heart rate.

24. A computerized veracity testing system according to claim 23 and wherein said hand engagement unit comprises:
multiple detection circuits for sensing skin conductivity; and
analysis circuitry operative to use outputs from said multiple detection circuits for providing an enhanced reliability indication of changes in skin conductivity.

25. A computerized veracity testing system according to claim 22 and wherein said hand engagement unit comprises:
multiple detection circuits for sensing skin conductivity; and
analysis circuitry operative to use outputs from said multiple detection circuits for providing an enhanced reliability indication of changes in skin conductivity.

26. A computerized veracity testing system according to claim 22 and wherein at least one of said subject observation subsystem and said at least one additional subject observation subsystem also comprises a selectable arm immobilizer for selectably immobilizing an arm of said subject.

27. A computerized veracity testing system according to claim 22 and wherein at least one of said subject observation subsystem and said at least one additional subject observation subsystem also comprises a motion detector for sensing breathing.

28. A computerized veracity testing system according to claim 27 and wherein at least one of said subject observation subsystem and said at least one additional subject observation subsystem comprises:
    multiple detectors, at least one of which is a camera, for sensing breathing; and
    analysis circuitry operative to use outputs from said multiple detectors for providing an enhanced reliability indication of changes in breathing rate.

29. A computerized veracity testing system according to claim 28 and wherein said hand engagement unit comprises:
    multiple detection circuits for sensing skin conductivity; and
    analysis circuitry operative to use outputs from said multiple detection circuits for providing an enhanced reliability indication of changes in skin conductivity.

30. A computerized veracity testing system according to claim 28 and wherein at least one of said subject observation subsystem and said at least one additional subject observation subsystem comprises:
    multiple detectors for sensing heart rate; and
    analysis circuitry operative to use outputs from said multiple detectors for providing an enhanced reliability indication of changes in heart rate.

31. A computerized veracity testing system according to claim 30 and wherein said hand engagement unit comprises:
    multiple detection circuits for sensing skin conductivity; and
    analysis circuitry operative to use outputs from said multiple detection circuits for providing an enhanced reliability indication of changes in skin conductivity.

32. A computerized veracity testing system according to claim 27 and wherein at least one of said subject observation subsystem and said at least one additional subject observation subsystem comprises:
    multiple detectors for sensing heart rate; and
    analysis circuitry operative to use outputs from said multiple detectors, at least one of which is a camera, for providing an enhanced reliability indication of changes in heart rate.

33. A computerized veracity testing system according to claim 32 and wherein said hand engagement unit comprises:
    multiple detection circuits for sensing skin conductivity; and
    analysis circuitry operative to use outputs from said multiple detection circuits for providing an enhanced reliability indication of changes in skin conductivity.

34. A computerized veracity testing system according to claim 22 and wherein at least one of said subject observation subsystem and said at least one additional subject observation subsystem comprises:
    multiple detectors, at least one of which is a camera, for sensing breathing; and
    analysis circuitry operative to use outputs from said multiple detectors for providing an enhanced reliability indication of changes in breathing rate.

35. A computerized veracity testing system according to claim 34 and wherein at least one of said subject observation subsystem and said at least one additional subject observation subsystem comprises:
    multiple detectors for sensing heart rate; and
    analysis circuitry operative to use outputs from said multiple detectors for providing an enhanced reliability indication of changes in heart rate.

36. A computerized veracity testing system according to claim 35 and wherein said hand engagement unit comprises:
    multiple detection circuits for sensing skin conductivity; and
    analysis circuitry operative to use outputs from said multiple detection circuits for providing an enhanced reliability indication of changes in skin conductivity.

37. A computerized veracity testing system according to claim 34 and wherein said hand engagement unit comprises:
    multiple detection circuits for sensing skin conductivity; and
    analysis circuitry operative to use outputs from said multiple detection circuits for providing an enhanced reliability indication of changes in skin conductivity.

38. A computerized veracity testing system comprising:
    a subject observation subsystem operative to provide an output representing at least one characteristic of a subject, said subject observation subsystem comprising:
        multiple different types of sensors providing outputs useful for ascertaining at least one of heart rate, breathing rate and skin conductivity; and
        a hand engagement unit comprising:
            a base element having separated finger support areas, each support area to support one finger of the subject;
            a plurality of physiological sensor contacts mounted in said finger support areas;
            selectably inflatable finger immobilization elements, each facing a respective finger support area for immobilizing a subject's fingers when his hand in operative engagement with the engagement unit; and
    an automatically operable computerized analysis subsystem responsive to said output of said subject observation subsystem for providing an indication relevant to veracity of the subject.

39. A computerized veracity testing system according to claim 38 and wherein said multiple different types of sensors include at least one of:
    a thermal camera and a motion detector, outputs of both of which are employed to ascertain breathing rate;
    a PPG sensor and a thermal camera, outputs of both of which are employed to ascertain heart rate and which may be also used to calculate breathing rate; and
    one or more EDA sensors and a motion detector, outputs of both of which are employed to ascertain skin conductivity.

40. A computerized veracity testing system according to claim 38, wherein said multiple different types of sensors includes a motion detector providing an output which is employed for ascertaining breathing rate.

* * * * *